(12) United States Patent
Felt

(10) Patent No.: US 8,949,738 B2
(45) Date of Patent: Feb. 3, 2015

(54) DRUG CALENDAR AND REMINDER SYSTEM

(75) Inventor: Michelle Felt, Randolph, NJ (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 270 days.

(21) Appl. No.: 13/277,760

(22) Filed: Oct. 20, 2011

(65) Prior Publication Data
US 2013/0104077 A1    Apr. 25, 2013

(51) Int. Cl.
*G06F 3/048* (2013.01)
*G06Q 10/00* (2012.01)
*G06Q 50/00* (2012.01)
*G06F 19/00* (2011.01)
*G06F 3/0481* (2013.01)
*G06Q 50/22* (2012.01)
*G06Q 50/24* (2012.01)

(52) U.S. Cl.
CPC .......... *G06F 19/3456* (2013.01); *G06F 19/322* (2013.01); *G06Q 50/22* (2013.01); *G06F 19/3487* (2013.01); *G06F 19/3406* (2013.01); *G06Q 50/24* (2013.01); *G06F 19/3418* (2013.01); *G06F 3/0481* (2013.01); *G06F 19/326* (2013.01); *Y10S 715/963* (2013.01)
USPC .................. 715/810; 715/963; 705/2; 705/3; 705/7.18

(58) Field of Classification Search
CPC ...... G06Q 50/22; G06Q 50/24; G06F 19/322; G06F 19/326; G06F 19/3406; G06F 19/3418; G06F 19/3456; G06F 19/3487
USPC .......................... 705/2, 3, 7.18; 715/810, 963
See application file for complete search history.

(56) References Cited

U.S. PATENT DOCUMENTS

| | | | |
|---|---|---|---|
| 6,466,236 B1* | 10/2002 | Pivowar et al. ............... | 715/835 |
| 6,985,869 B1* | 1/2006 | Stoll et al. .......... | 705/2 |
| 8,006,197 B1* | 8/2011 | Nevill-Manning et al. .... | 715/788 |
| 2002/0021828 A1* | 2/2002 | Papier et al. .................. | 382/128 |
| 2002/0022973 A1* | 2/2002 | Sun et al. .......... | 705/3 |
| 2004/0243445 A1* | 12/2004 | Keene ............... | 705/2 |
| 2004/0247748 A1* | 12/2004 | Bronkema ................... | 426/106 |
| 2005/0102201 A1* | 5/2005 | Linker et al. ................... | 705/27 |
| 2006/0155542 A1* | 7/2006 | Vimegnon et al. ............ | 704/260 |
| 2006/0248078 A1* | 11/2006 | Gross et al. ........ | 707/5 |
| 2007/0130129 A1* | 6/2007 | Wagle .............. | 707/3 |
| 2007/0168228 A1* | 7/2007 | Lawless ........... | 705/2 |
| 2007/0226033 A1* | 9/2007 | LoPresti ........... | 705/9 |
| 2007/0238936 A1* | 10/2007 | Becker ............... | 600/300 |
| 2007/0282476 A1* | 12/2007 | Song et al. .......... | 700/100 |
| 2008/0013705 A1* | 1/2008 | Yoffie et al. ............ | 379/201.12 |
| 2009/0036828 A1* | 2/2009 | Hansen et al. ................. | 604/66 |
| 2009/0255153 A1* | 10/2009 | Mori et al. ...... | 40/107 |
| 2009/0281835 A1* | 11/2009 | Patwardhan et al. ............ | 705/3 |
| 2010/0305749 A1* | 12/2010 | Coe ................ | 700/231 |
| 2011/0015947 A1* | 1/2011 | Erry et al. ........ | 705/3 |
| 2011/0264696 A1* | 10/2011 | Selaniko ....... | 707/770 |
| 2012/0160716 A1* | 6/2012 | Chan et al. .................. | 206/216 |

* cited by examiner

*Primary Examiner* — Eric J Bycer

(57) ABSTRACT

A drug calendar and reminder system is provided which allows for a user to be reminded when and how to take regularly scheduled drugs. The drug calendar and reminder system allows a user to input one or more drugs including their dosage instructions and schedule, and creates interactive reminders to facilitate the regular taking of these drugs. The drug calendar and reminder system can be further configured to receive content from content providers, such as drug interaction services, drug databases, doctors, and pharmacies such that a user can readily access information from these providers as needed. The drug calendar and reminder system can also be configured to compile the user's drug information, and can be configured to allow content providers access to this information.

23 Claims, 18 Drawing Sheets

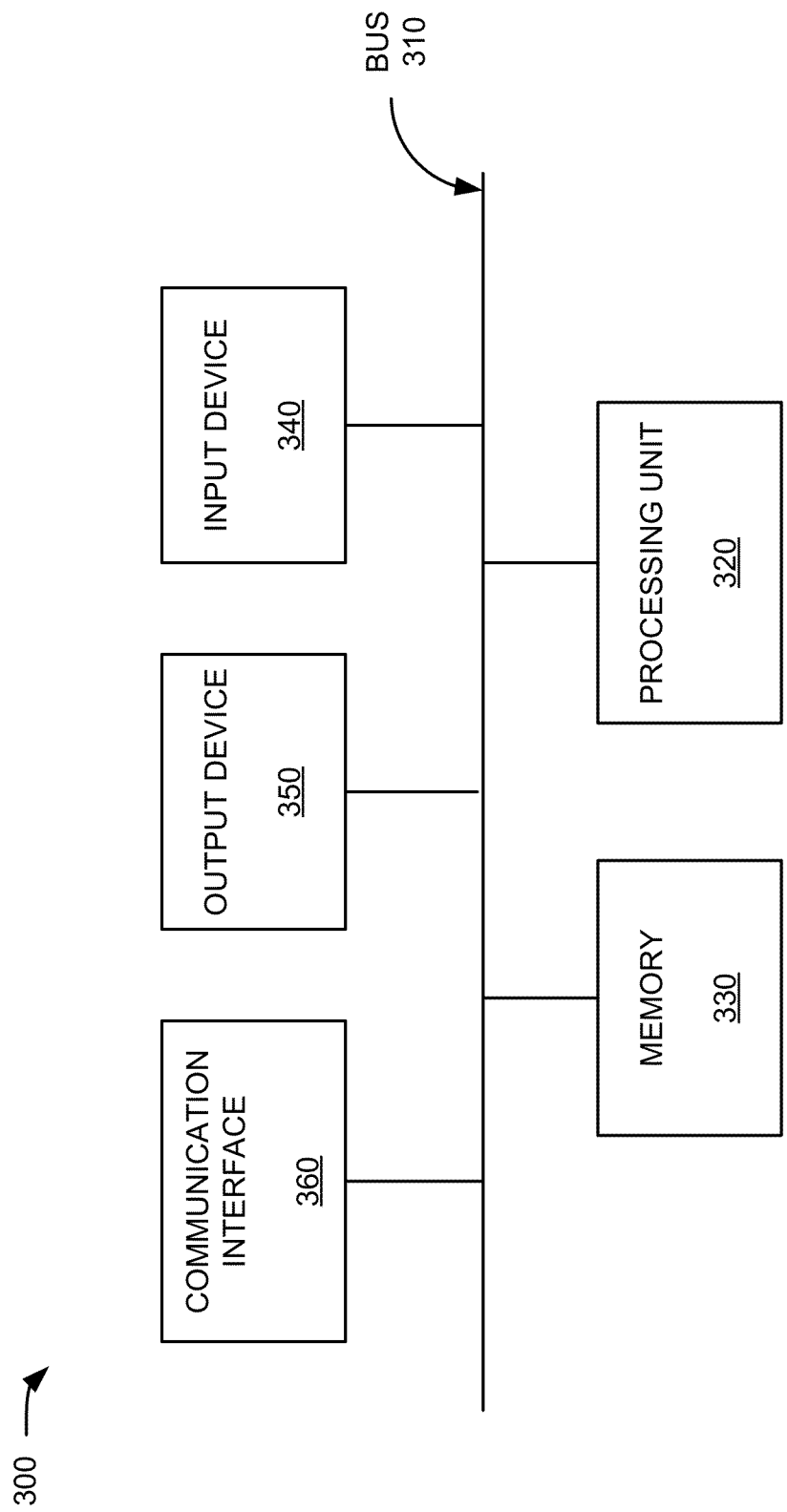

DRUG CALENDAR AND REMINDER SYSTEM

BACKGROUND

Proper ingestion of drugs, such as prescription medications and vitamins, with the correct timing, frequency, and environment can be difficult to remember on a regular basis. Beyond proper ingestion, remembering whether drugs have been taken at their scheduled times, being able to recite all of the drugs to concerned parties, such as pharmacists or doctors, and remembering to administer drugs for more than one person by a caregiver, for example, can also be difficult.

BRIEF DESCRIPTION OF THE DRAWINGS

FIG. 3 is a diagram of example components of a device that may be used within the environment of FIG. 2;

DETAILED DESCRIPTION OF PREFERRED EMBODIMENTS

The following detailed description refers to the accompanying drawings. The same reference numbers in different drawings may identify the same or similar elements.

The description to follow will describe drugs generically, and is intended to include prescription medications, vitamins, over-the-counter medications, special diets, injections, or other types of ingestions, which may need reminders. While the description will focus on drug consumption, the description is not so limited and may apply to other types of content, such as daily, weekly, or monthly reminders for other events like appointments, chores, or the like. For example, weekly reminders of soccer practices, study groups, etc. can be set up in implementations.

An implementation, described herein, may use one or more communication policies to determine when and how drug information is provided on a device. The communication policies may be set, by a user of the device, a provider of the drug information, or a provider of other services, to provide drug information in a manner that is beneficial and convenient to the user or the provider. For example, the drug information may be coordinated between a user and a provider, such as a doctor or pharmacy, depending on timing for availability of information and convenience for each party.

Figure 1:
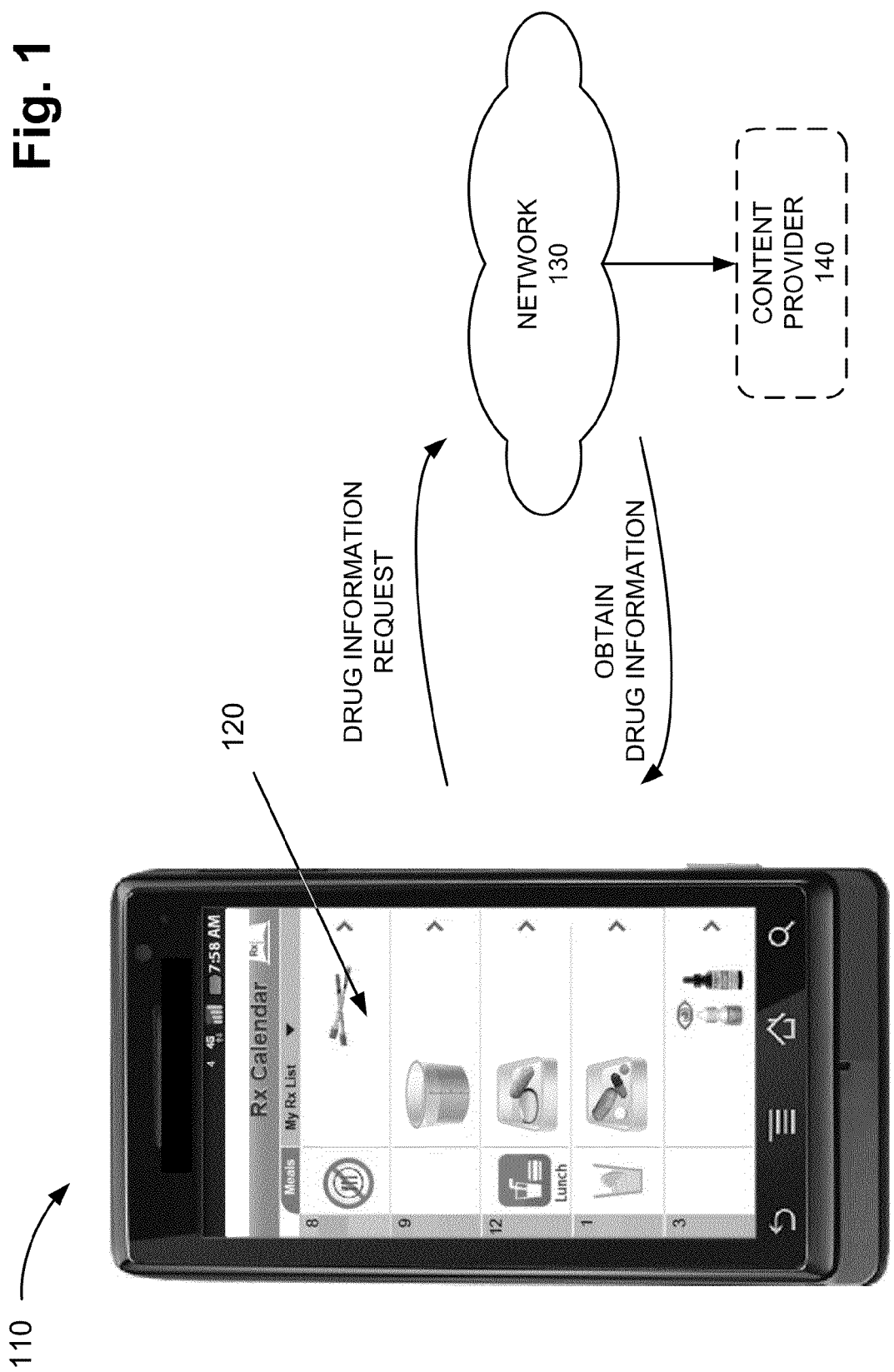
FIG. 1 is a diagram of an overview of an implementation described herein.

FIG. 1 is a diagram of an overview of an implementation described herein. As shown in FIG. 1, a user of a device 110 may use the device 110 to request and obtain drug information from a content provider 140 through a network 130. For example, the user may access a list of drugs made available by a content provider 140 through the use of a network 130. In response to a selection of a particular drug from the list of drugs from the content provider 140, a user through their device 110 may request drug information from the list, and obtain the drug information accordingly.

Also, the manner in which the drug information is obtained can be set according to communication policies previously set between the user and content provider 140, such as immediate, daily, or weekly downloads of the drug information. This drug information may be used to populate a user interface 120 of a drug calendar and reminder system, and provide a visual drug calendar displaying, for example, visual representations of each drug, such as a small white pill and a larger blue and green capsule, along with the condition meant for the drug taking, such as a lunch icon, or any information relevant to a drug information request.

A drug calendar and reminder system that reminds a user of when and how to take regularly-scheduled drugs is provided. In one implementation, the drug calendar and reminder system may refer to software executing on a device, such as device 110. In another implementation, the drug calendar and reminder system may refer to software executing on both a device, such as device 110, and a server device, such as a server device associated with content provider 140. In yet another implementation, the drug calendar and reminder system may refer to software executing on a server device, such as a server device associated with content provider 140, that provides visual aspects on a device, such as device 110.

The drug calendar and reminder system may allow a user to input one or more drugs including their dosing instructions and schedules, and may create calendars and interactive reminders to facilitate the regular taking of these drugs. For example, the drug calendar and reminder system described herein allows for a graphical user interface to be populated by image representations of each drug compiled into groups and times such that visual reminders can be shown either as a calendar with multiple entries or as one or more reminders.

Another example of the drug calendar and reminder system allows for the visual reminder to be updated and revised as a day goes on. For example, if a user decides to take the drugs assigned to a particular time, then the drug calendar and reminder system can change the visual representations in the drug calendar to show that the drugs were taken, and update the reminder to not remind the user about the drugs assigned to that particular time again. Alternatively or additionally, the drug calendar and reminder system can allow for the visual representations of drugs to show only a portion of the drugs taken and set up a visual reminder also reflecting this drug taking status reminding the user to take the remaining portion of the drugs at a later time.

Also, the drug calendar and reminder system allows for interaction between content providers 140 and a user of a device 110. By allowing a doctor, for example, to access a patient's records and be able to provide notes, gather information or generally communicate through a network directly into a drug specific application on a device 110, a user of device 110 can have access to doctors and vice-versa—all centralized into an easily accessible visual drug calendar and reminder system. The drug calendar and reminder system can also be configured to compile the user's drug information, and can allow content providers 140 access to this compiled information, if desired. The drug calendar and reminder system can be further configured to receive content from content providers 140, such as information regarding drug interactions, drug lists, doctors, and pharmacies.

Figure 2:
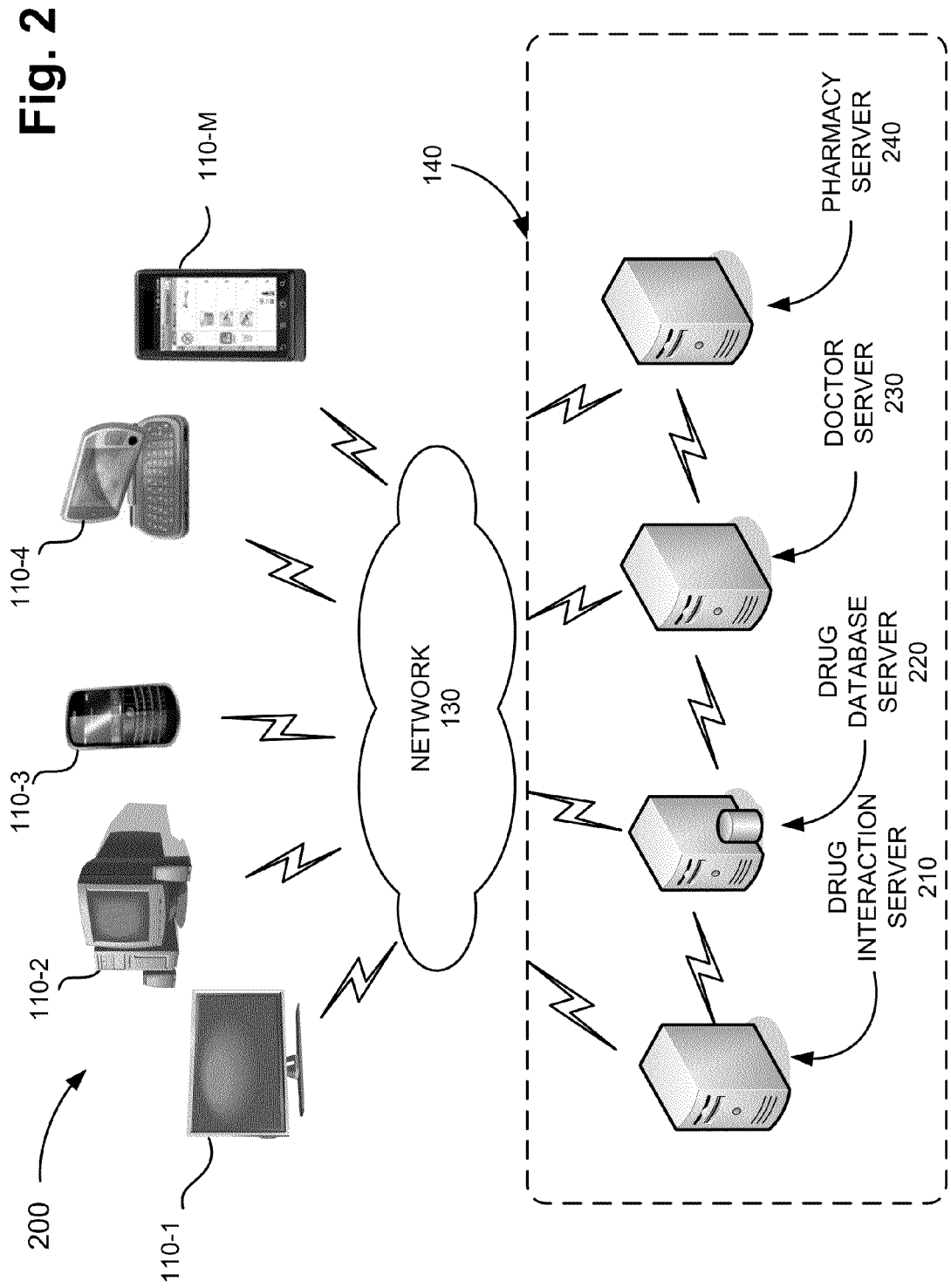
FIG. 2 is a diagram that illustrates an example environment in which systems or methods, described herein, may be implemented.

FIG. 2 is a diagram that illustrates an example environment 200 in which systems or methods, described herein, may be implemented. As shown in FIG. 2, environment 200 may include devices 110-1, 110-2, . . . 110-M (where M≥1) (collectively referred to as "devices 110," and individually as "device 110"), and one or more content providers 140, such as a drug interaction server 210, a drug database server 220, a doctor server 230, or a pharmacy server 240, all of which can be connected to a network 130. While FIG. 2 shows a particular number and arrangement of devices, in practice, environment 200 may include additional, fewer, different, or differently arranged devices than are shown in FIG. 2. For example, each example content provider 210, 220, 230, or 240 may be implemented as multiple, possibly distributed, devices. Alternatively, two or more of the example content provider 210, 220, 230, or 240 may be implemented within a single device.

Device 110 may include any device capable of communicating via a network, such as network 130. For example, device 110 may correspond to a television 110-1 optionally including a set top box, an internet device, or a gaming system; a personal computer 110-2 including desktops, all-in-ones, laptops, tablets; or a mobile communication device 110-3, 110-4, and 110-M (e.g., a mobile phone, a smart phone, a personal digital assistant (PDA), or another type of portable device.

Network 130 may generally include logic to provide wireless access for devices 110. Through a network 130, devices 110 may, for instance, communicate with one another (e.g., via a voice call), access services through IP network, and/or complete telephone calls through a traditional telephone network, such as a public switched telephone network (PSTN). Network 130 may be a network that provides a wireless (radio) interface to devices 110 using the $3^{rd}$ generation (3G) mobile telecommunications standards. An implementation of 3G network may include one or more elements through which devices 110 may wirelessly connect to receive telecommunication services. Network 130 may be a network that provides a wireless (radio) interface to devices 110 using the $4^{th}$ generation (4G) mobile telecommunications standards. An implementation of 4G network 130 may include one or more elements through which devices 110 may wirelessly connect to receive telecommunication services.

Drug interaction server 210 may include a server device (or a collection of server devices) that can provide drug interaction information on the drugs being taken by a user. For example, the drug interaction information may indicate whether one or more of a user's drugs interacts safely or harmfully with one or more of the user's other drugs. The drug interaction information may be provided by doctors, nurses, pharmacists, pharmaceutical companies, or independent companies or groups that have an interest in offering the drug interaction information for profit or for user safety and liability prevention.

Drug database server 220 may include a server device (or a collection of server devices) that stores or maintains a compilation of drug information. For example, drug database server 220 may include information from one or more public or private databases, such as pharmacy specific databases, pharmaceutical companies' databases, or other medication information databases.

Doctor server 230 may include a server device (or a collection of server devices) that stores medical information for a doctor and is accessible by an entire doctor's office, associated doctors' offices, nurses, and/or staff members. The information may include many different types of data regarding a user, such as login information (e.g., user identifier and password), billing information, address information, types of services that have been provided (or are scheduled to be provided) to the user, a list of prescription and non-prescription drugs taken by the user, a list of illness, diseases, or other maladies suffered by the user, a list of previously taken drugs that the user no longer takes, a list of allergies or other complications that the user may suffer from, feedback from the user, a device identifier (e.g., a mobile device identifier, a personal computer identifier) for devices used by the user, information regarding a drug calendar and reminder system associated with the user, etc. Additionally, the doctor server 230 can be connected to the drug database server 220 and/or the drug interaction server 210 along with the device 110, so that the doctor server 230 may provide information to the user using other content providers 140 as needed or desired.

Pharmacy server 240 may include a server device that can communicate with a user through their device 110 and may be used to provide certain information to the user. The information may include many different types of data regarding a user, such as login information (e.g., user identifier and password), billing information, address information, a list of prescription and non-prescription drugs taken by the user, a list of illness, diseases, or other maladies suffered by the user, a list of previously taken drugs that the user no longer takes, a list of allergies or other complications that the user may suffer from, feedback from the user, a device identifier (e.g., a mobile device identifier, a personal computer identifier, etc.) for devices used by the user, information regarding the drug calendar and reminder system associated with the user, etc. Additionally, the pharmacy server 240 can be connected to the doctor server 230, the drug database server 220, and/or the drug interaction server 210 along with the device 110 through the network 130, so that the pharmacy server 240 can provide information to the user using other content providers 140 as needed or desired.

Although FIGS. 1 and 2 show example components, other implementations may contain fewer components, different components, differently arranged components, or additional components than depicted in FIGS. 1 and 2. Alternatively, or additionally, one or more components may perform one or more tasks described as being performed by one or more other components.

FIG. 3 is a diagram of example components of a device 300 that may be used within the environment of FIG. 2. Device 300 may correspond to a device 110 or a content provider 140, such as drug interaction server 210, drug database server 220, doctor server 230, pharmacy server 240, or any other content provider 140 desirable in a reminder system, such as the drug calendar and reminder system described above. Each of content providers 140, including the drug interaction server 210, the drug database server 220, the doctor server 230, and the pharmacy server 240, may include one or more devices 300.

As shown in FIG. 3, device 300 may include a bus 310, a processing unit 320, a memory 330, an input device 340, an output device 350, and a communication interface 360. In another implementation, device 300 may include additional, fewer, different, or differently arranged components.

Bus 310 may include a path, or collection of paths, that permits communication among the components of device 300.

Processing unit 320 may include one or more processors or microprocessors that interpret and execute instructions. Additionally or alternatively, processing unit 320 may be implemented as or include one or more application specific integrated circuits (ASICs), field programmable gate arrays (FPGAs), or another type of processor that interprets and executes instructions.

Memory 330 may include memory or secondary storage. For example, memory 330 may include a random access memory (RAM) or another type of dynamic storage device that stores information or instructions for execution by processing unit 320. Additionally, or alternatively, memory 330 may include read only memory (ROM) or another type of static storage device that stores static information or instructions for use by processing unit 320. Additionally, or alternatively, memory 330 may include a magnetic storage medium, such as a hard disk drive, or a removable memory, such as a flash memory.

Input device 340 may include a mechanism that permits an operator to input information to device 300, such as a control button, a keyboard, a keypad, a touch pad, one or more biometric mechanisms, or another type of input device. Output device 350 may include a mechanism that outputs information to the operator, such as a light emitting diode (LED), a display, a speaker, or another type of output device.

Communication interface 360 may include a component that permits device 300 to communicate with other devices using any transceiver-like mechanism that enables device 300 to communicate with other devices (e.g., devices 110), networks (e.g., network 130), or content providers 140. In one implementation, communication interface 360 may include a wireless interface, a wired interface, or a combination of wireless interface and a wired interface.

Device 300 may perform certain operations, as described in detail below. Device 300 may perform these operations in response to processing unit 320 executing software instructions contained in a computer-readable medium, such as memory 330. A computer-readable medium may be defined as a non-transitory memory device. A memory device may include space within a single physical memory device or spread across multiple physical memory devices.

The software instructions may be read into memory 330 from another computer-readable medium, such as a storage device, or from another device via communication interface 360. The software instructions contained in memory 330 may cause processing unit 320 to perform processes that will be described later. Alternatively, hardwired circuitry may be used in place of or in combination with software instructions to implement processes described herein. Thus, implementations described herein are not limited to any specific combination of hardware circuitry and software.

Figure 4A:
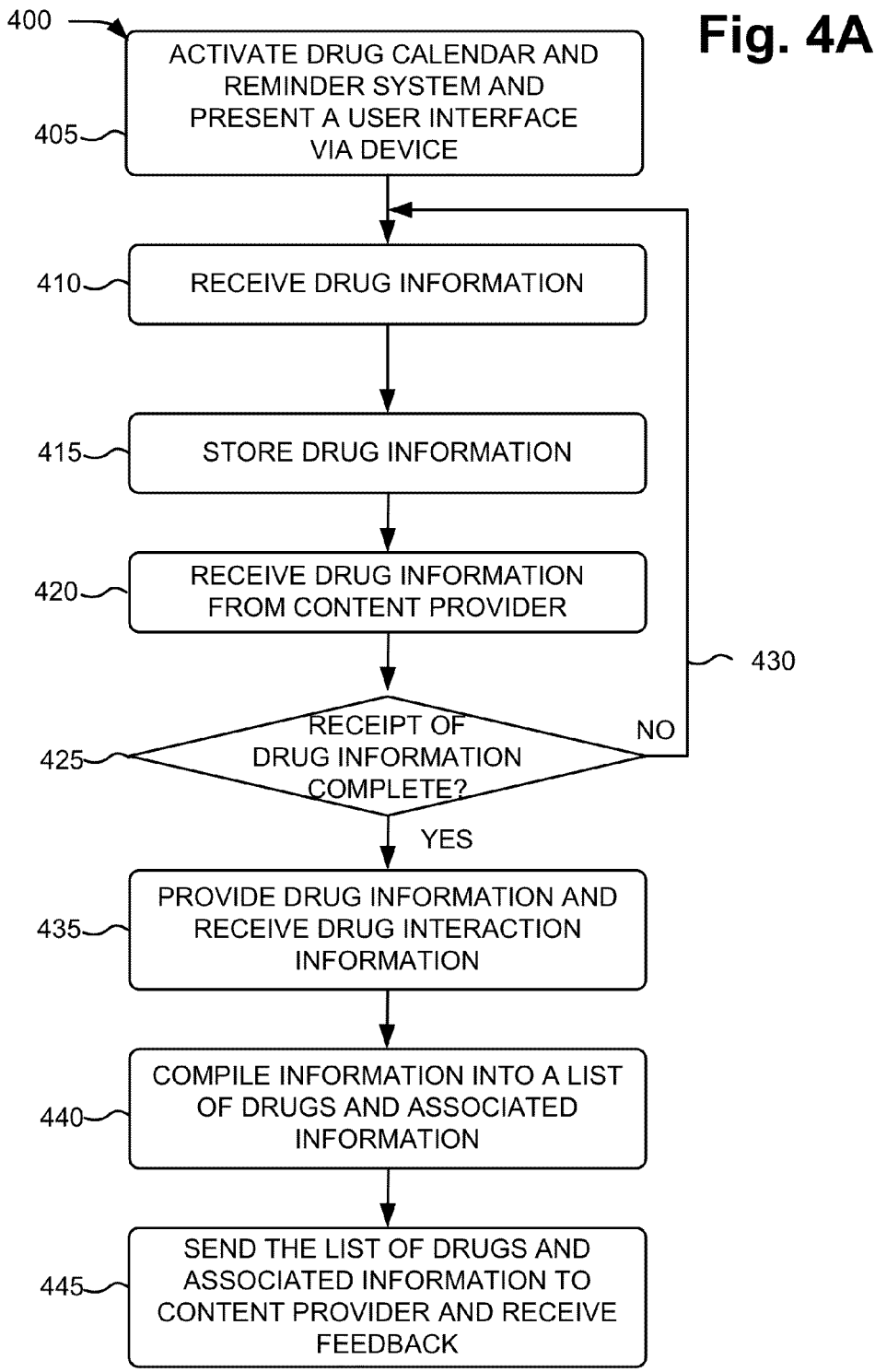
FIG. 4A is a flowchart of an example process for creating entries into an example system described herein.
Figure 4B:
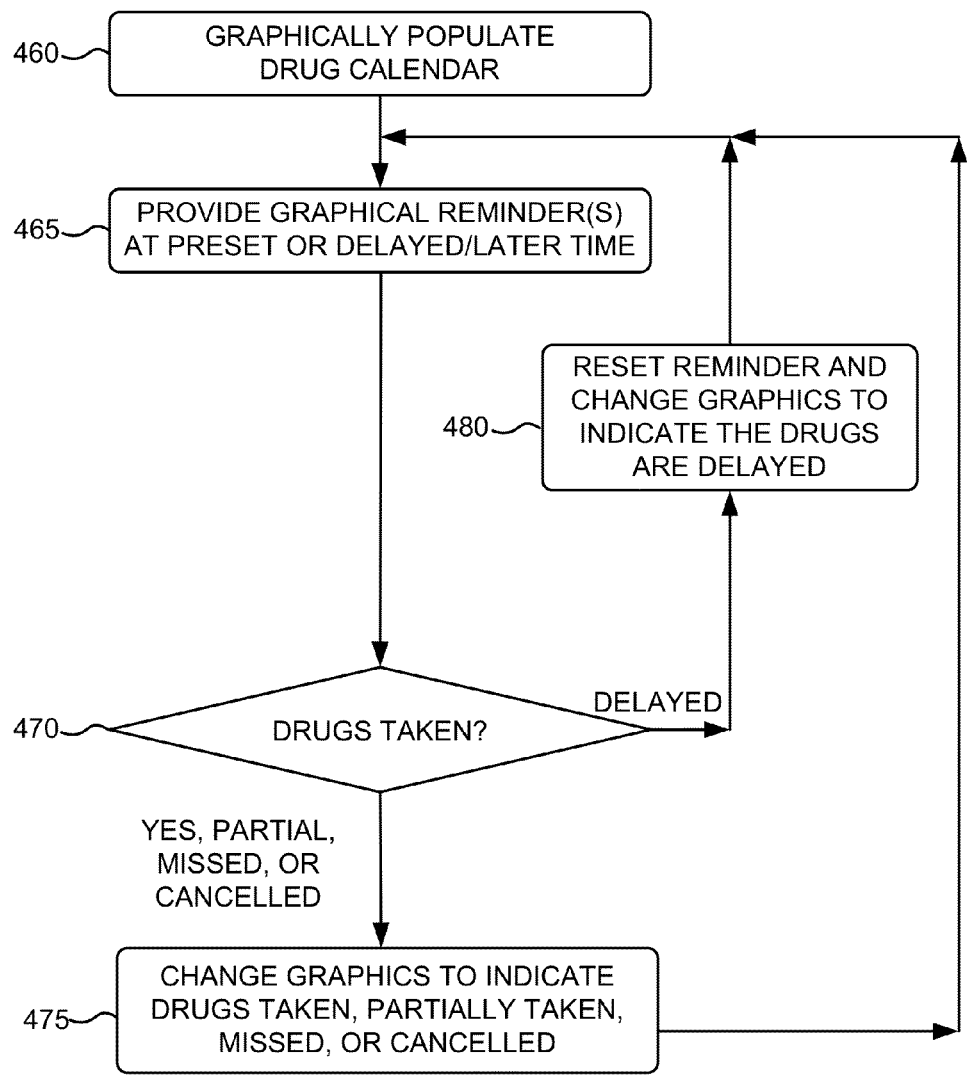
FIG. 4B is a flowchart of an example process for using an example system described herein.

FIGS. 4A and 4B illustrate an example process 400 for creating entries in an example system and an example process 450 for using an example system, respectively. These example processes allow for providing and interacting with an example drug calendar and reminder system. In one implementation, processes 400 and 450 may be performed by one or more components of a device 110, such as a processing unit 320 of device 110. In another implementation, one or more blocks of process 400 or 450 may be performed by one or more components of another device (e.g., one or more content providers 140) or a group of devices including or excluding device 110. Processes 400 and 450 will be described with corresponding references to example user interfaces illustrated in FIGS. 5A-14.

Process 400 may include activating drug calendar and reminder system, and presenting, via a display associated with a device 110, a user interface to permit a user to specify a drug (block 405). Assume, for this example process 400, that the drug calendar and reminder system refers to an application stored on device 110, or on a server device of content provider 140 that is accessible by device 110. For example, a user of device 110 may activate the drug calendar and reminder system, stored in device 110 in a standard manner, such as by selecting an icon (or another type of identifier) associated with the drug calendar and reminder system, selecting the name of the drug calendar and reminder system from a list, or using another method of selection, where upon activation occurs and a user interface is presented.

Process 400 may include receiving drug information via a display associated with the device 110 (block 410). For example, device 110 may present a user interface 120 for permitting a user to specify a drug and receiving a user's input defining the drug.

Figure 5A:
FIG. 5A is a diagram of an example user interface for entering new drugs into an example system described herein.

FIG. 5A is a diagram of an example user interface for entering new drugs into an example system. As illustrated in FIG. 5A, the drug calendar and reminder system can provide an interactive field 510 in which a user can enter a drug name or a portion of a drug name. Based on the user's input of at least a portion of a drug name, the drug calendar and reminder system can populate a selection of choices for the user's further selection. For example, as shown in FIG. 5A, there can be several entries for a single drug name. In this example, the "Tegretol"® entry in FIG. 5A is illustrated as having three different types with different dosages or release compositions (e.g., 5MG, 10MG, XR), along with different pill shapes, pill colors, and pill sizes. Using this example, the drug calendar and reminder system can allow the user to select among the different images, such as the "Tegretol® TAB 10MG" which can be visually differentiated from the "Tegretol® XR TAB 5MG" as the two drugs look different from their drug identifying images. This can be useful for users who would rather identify a picture of a drug rather than a specific name. The user can then select one of the drugs from the interactive entry box 510. For example, a user of device 110 may select among the choices provided in a standard manner, such as by selecting a graphical image (or another type of identifier) associated with the drug of choice, selecting the name of the drug from a list, or using another method of selection.

Figure 5B:
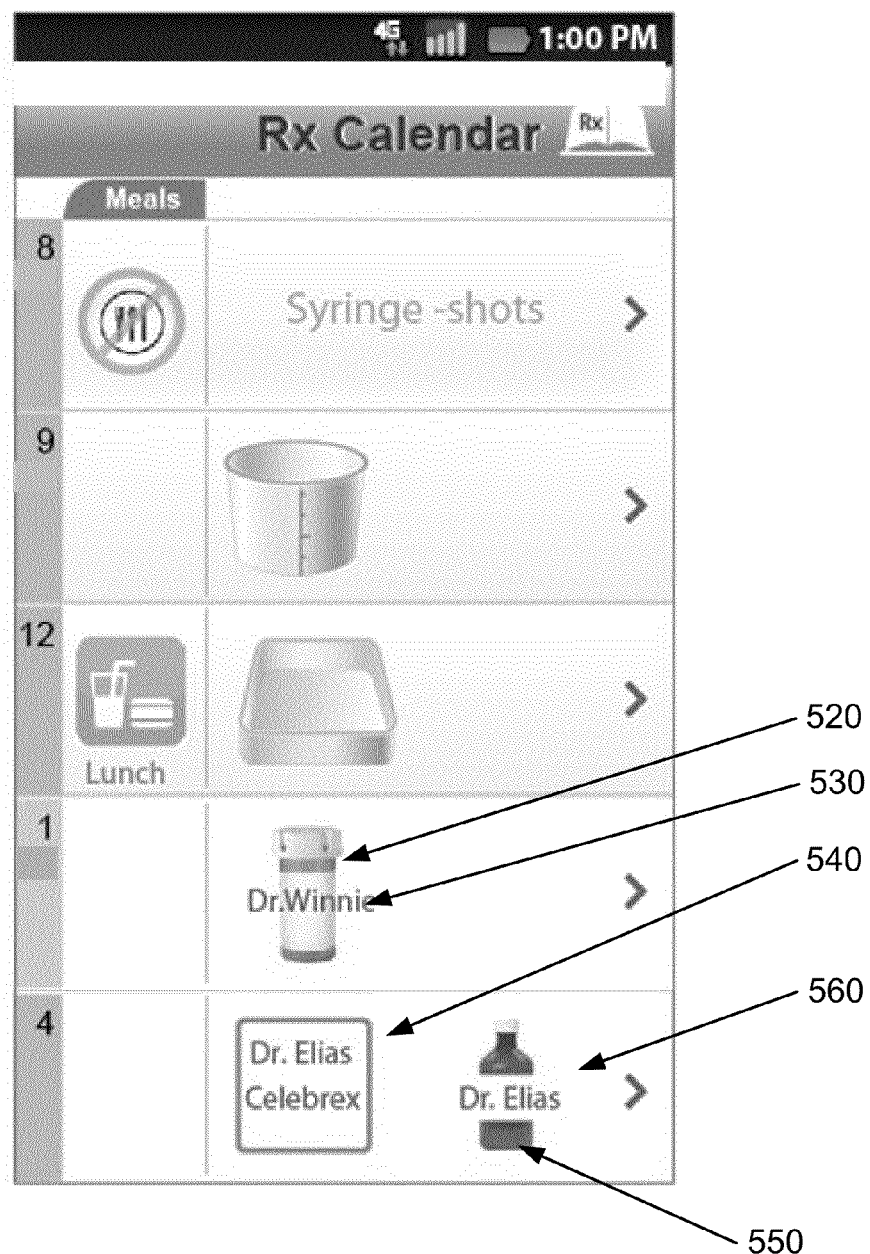
FIG. 5B is a diagram of another example user interface for entering new drugs into an example system described herein.

Alternatively, as envisioned in further examples, the drug calendar and reminder system can receive drug information from the user if the user wants to: (a) select a generic picture; or (b) enter a name not in the database. FIG. 5B is a diagram of another example user interface for entering new drugs into an example system. As shown in FIG. 5B, the user can select a generic picture, such as bottle 520, box 540, or liquid container 550; and can enter a designating name or label 530, 540, 560. Alternatively, a box 540, a different bottle 550 with a label 560, or even a specific pill (not shown) can be entered along with a label or without a label. For example, a specific pill image can be selected and "dragged and dropped" from a list of generic pill images resembling the appearance of the drug that the user wants for a reminder, where the generic pill image can have the same general shape, color, and design as the pill that the user actually takes.

Figure 6A:
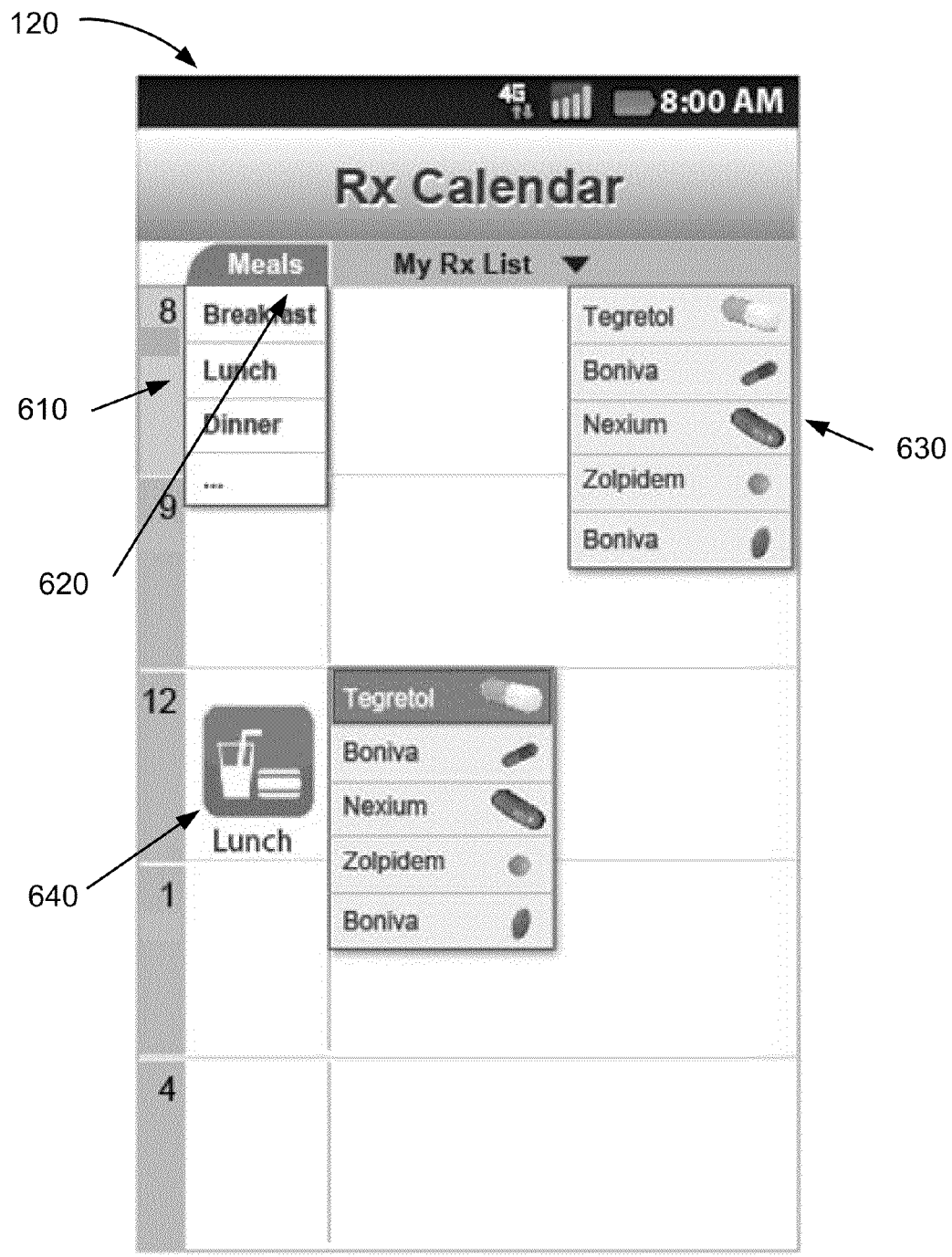
FIG. 6A is a diagram of another example user interface for selecting drugs, times, and conditions for an example system described herein.

FIG. 6A is a diagram of another example user interface for selecting drugs, times, and conditions for an example system described herein. As shown in FIG. 6A, the drug calendar and reminder system can receive additional drug information from the user through interaction with user interface 120. For example, as illustrated in FIG. 6A, the drug calendar and reminder system can receive scheduling information, such as a time 610, and dosing information, such as one or more pills from a drug list 630, a meal 620, or a meal and drink 640, by selecting an identifier of information, such as an icon associated with the selection, information from a list, or another form of information presentation.

Returning to FIG. 4A, process 400 may include storing drug information (block 415). For example, an input received from the user via the example user interface can be stored in memory associated with the device 110, such as within internal mobile device memory, removable memory, or server memory.

Process 400 may include receiving drug information from a content provider (block 420). For example, the drug calendar and reminder system can receive drug information from a content provider 140, such as a doctor server 230 or a pharmacy server 240. In one implementation, the drug calendar and reminder system can receive information from a doctor server 230 regarding patient-doctor specific instructions, such as dosing warnings based on the patient's medical history, reminders on refills, or reminders on follow up visits.

Figure 6B:
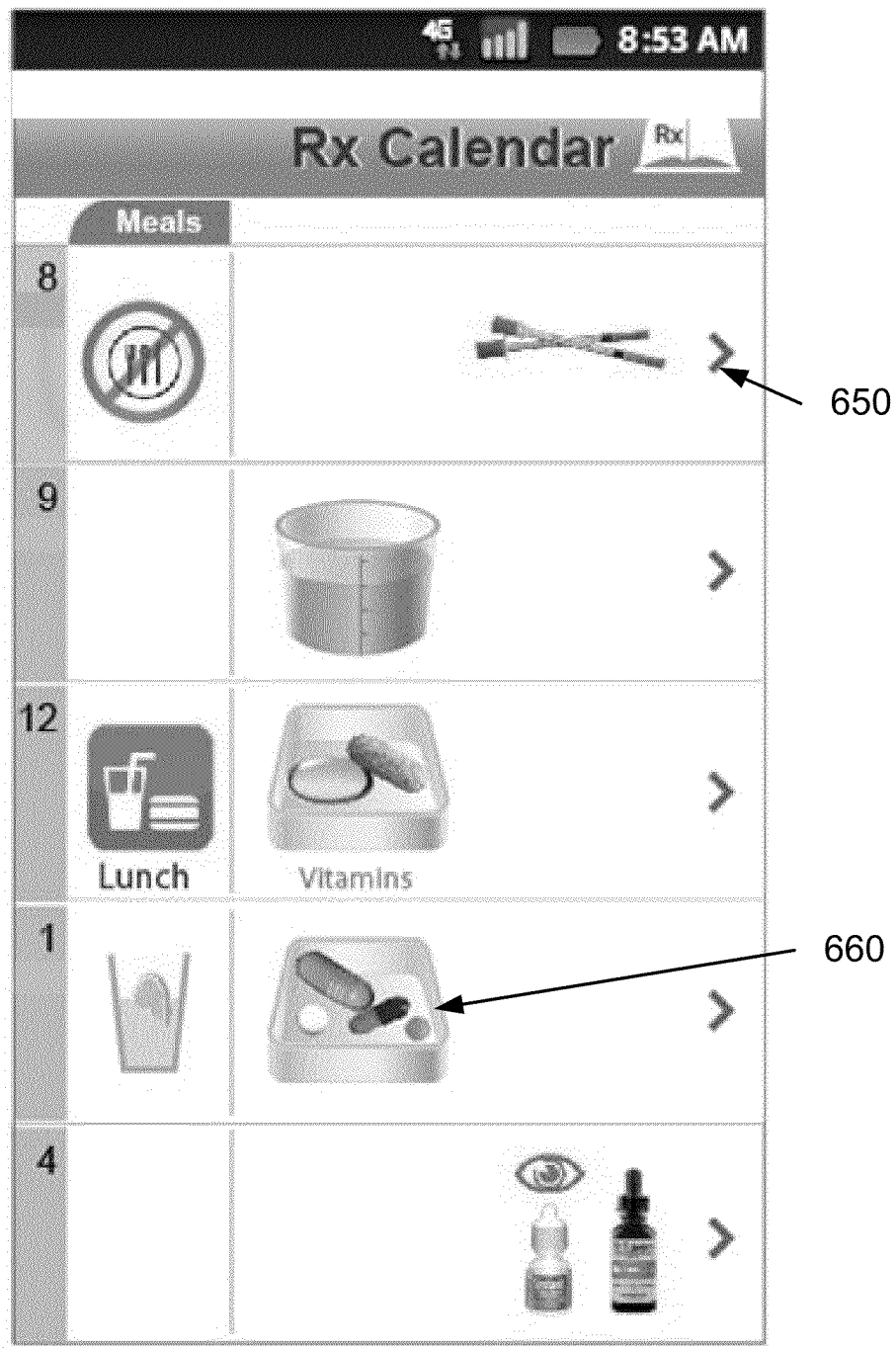
FIG. 6B is a diagram of another example user interface for selecting a link for an example system described herein.

The receipt of drug information from a content provider 140 can be accessed, for example, as illustrated in FIG. 6B. FIG. 6B is a diagram of another example user interface for selecting a link for an example system described herein. In FIG. 6B, an identifier of an example link 650 can be used to provide a user with direct access to drug information received from a content provider 140 or from any other source providing drug information. The drug calendar and reminder system can operate fully without receiving drug information from a content provider 140. Drug information can be stored in memory associated with the device 110, such as within internal mobile device memory, removable memory, or server memory.

Returning to FIG. 4A, process 400 may include determining whether the receipt of drug information is complete (block 425). For example, the drug calendar and reminder system may prompt the user to find out whether information regarding more drugs needs to be entered. If more drugs are to be entered (block 425—No), then blocks 415 and 420 may be repeated until the user is satisfied with the drug information inputted, as shown in line 430.

Process 400 may include providing drug information and receiving drug interaction information (block 435). For example, the drug calendar and reminder system can provide information to and receive information from a drug interaction server 210 regarding drug interactions based upon the drug information received in blocks 415 and 420. If, for example, the drug interaction server 210 determines that there is a potential adverse interaction between the drugs, then the drug interaction server 210 may send a warning or information concerning the potential adverse interaction to a processor of a device 110. Additionally or alternatively, the drug interaction server 210 may send this information to a content provider 140, who in turn can send a warning or information concerning the potential adverse interaction to the processor of the device 110. On the other hand, if the drug interaction server 210 finds no potential adverse interaction between the drugs, then the drug interaction server 210 can send a notification of safety or other notice.

Process 400 may include compiling a list of drugs and the frequencies of each drug's use (block 440). For example, the drug calendar and reminder system may gather the drugs and the drug information into a list that can have a separate window for display on device 110. For example, this list may be formatted for displaying on the device 110, which can be similar to the graphical list of FIG. 6B, which graphically illustrates each of the drugs to be taken on a particular day, where the drugs are identified by their individual appearances. Additionally or alternatively, a list with text similar to FIG. 14, which lists the drug name, dosage, and frequency (e.g., "TEGRETOL 10 MG 3/DAY," "BONIVA 10 MG 1/MONTH," etc.) can be compiled in a form that can be quickly read.

Process 400 can allow for changes to the compiled list of drugs. The compiled list can allow the user to review the list and make changes to the compiled list, and can use the same or a similar interface to user interface 120 illustrated in FIGS. 5A, 5B, and 6A. For example, if a drug was prescribed after the calendar was made, then the drug calendar and reminder system can receive additional drug information via interface 120 of FIGS. 5A, 5B, and 6A of a device 110 (block 415). Receipt of additional drug information can be similar to the portion of process 400 that occurs when receipt of drug information is found to be incomplete (block 425—No).

Process 400 may include sending the compiled list to a content provider 140 and receiving feedback (block 445). For example, this list may be transmitted to a content provider 140 by transmitting the list via email, text, or other transmission method to a content provider 140, where the content provider 140 can review the list and send feedback. The feedback can include feedback like suggestions not to take two drugs from the list too close in time to each other, changing a prescription based upon other prescribed medicines in the list, etc. The feedback can be received by device 110 for review via a link or a notification, where the feedback information's urgency can also be received by the device 110. For example, doctor server 230 can receive a list of drugs from device 110 and allow a doctor to review the list, then the doctor can provide feedback in the form of a warning about two drugs shown in the same "tray" (e.g., one of the capsules and one of the tablets in tray 660 in FIG. 6B) not being safe to take simultaneously and needing a preset number of hours between taking one drug and another drug.

In FIG. 4B, process 450 may include an example process for using the drug calendar and reminder system. The information compiled in block 440 can be provided to the drug calendar and reminder system. For example, between the last block of FIG. 4A and the first block of FIG. 4B, the drug calendar and reminder system can be resumed at a later time if the entry of the information is desired to be separate from a calendaring and reminding portion of the drug calendar and reminder system.

Process 450 may graphically populate the drug calendar and reminder system on a device 110, such that graphical calendar(s) and reminder(s) can be shown to the user of device 110 (block 460). This graphical population can be done by receiving an instruction from a user of a device 110 to make a calendar, such as by selecting an icon or an item from a list, preparing a calendar reminder accordingly using a processor on the device 110 or a processor on a server device, and visually displaying the calendar or reminder on the device 110. An example embodiment may include a graphical user interface pop-up screen reminder of a calendar or reminder as further illustrated in FIGS. 7, 8A, and 8B, respectively.

Figure 7:
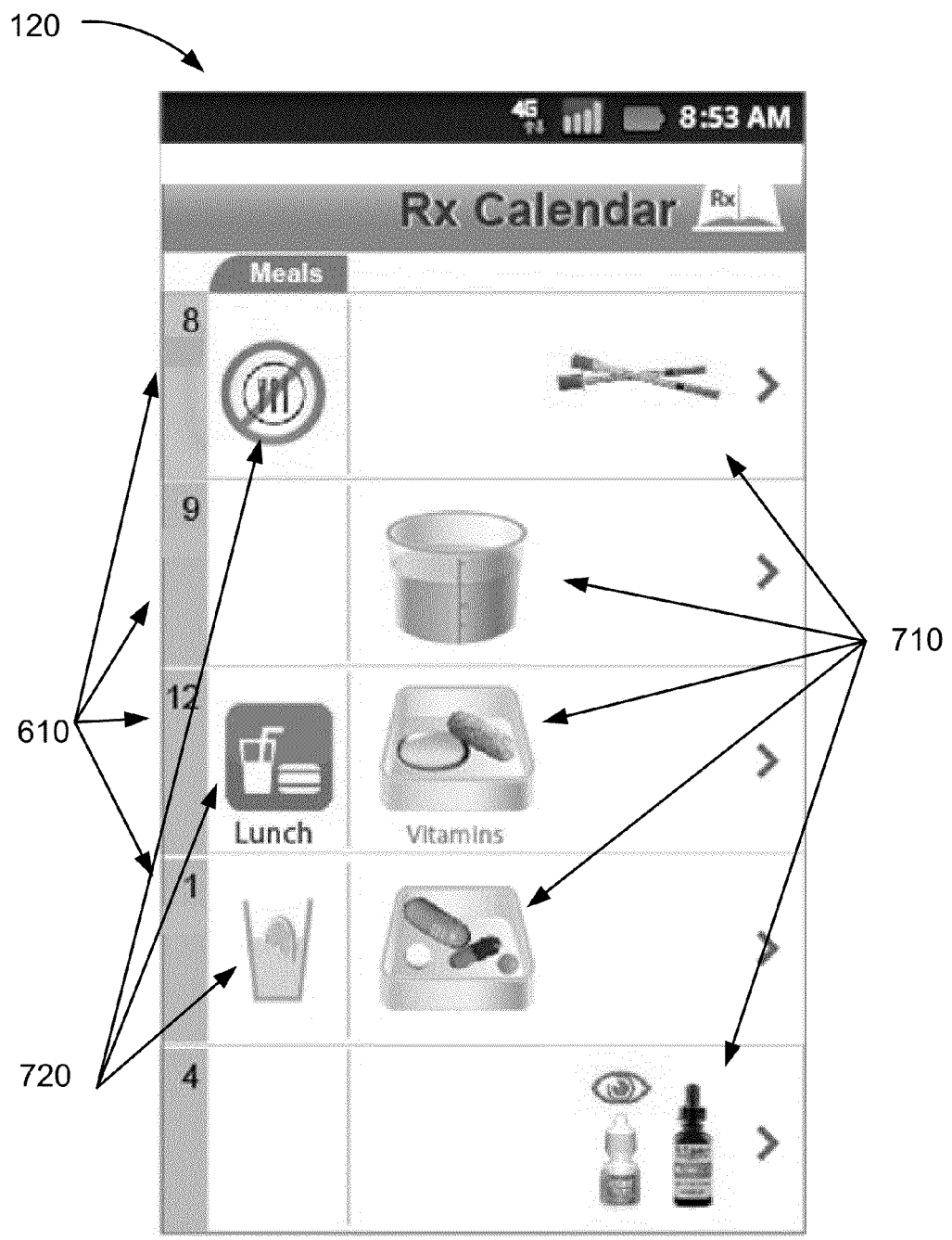
FIG. 7 is a diagram of another example user interface displaying a calendar entry for an example system described herein.

FIG. 7 is a diagram of another example user interface displaying a calendar entry for an example system described herein. As illustrated in FIG. 7, an example user interface 120 illustrates a calendar day entry for various identifiers of drug information 710 scheduled for particular times (see the time identifiers 610) with particular food and drink conditions (see food and drink condition identifiers 720) of the user interface. For example, on this calendar day entry illustrated in FIG. 7, the following calendar should be followed with the appropriate drugs taken or administered: at 8, drugs via syringes with no food; at 9, a vial with liquid with no food requirements; at 12, two pills labeled "Vitamins" with lunch; at 1, four pills (two capsules and two tablets) with juice; and at 4, two eye drops with no food requirements.

As illustrated in FIG. 7, each of the images of the drugs resembles how the actual drugs appear. For example, the syringes taken at 8 would really be two syringes for administration of an injection, while the liquid taken at 9 may be illustrated as taking up that same amount in a similar cup, etc. By providing the drugs in a visual manner, where each drug, container, and ingestion image 710 in the drug calendar and reminder system user interface 120 resembles what the actual drug, container, or ingestion method looks like, the drug calendar and reminder system can provide simple visual cues to ensure that the correct drug is taken.

Figure 8A:
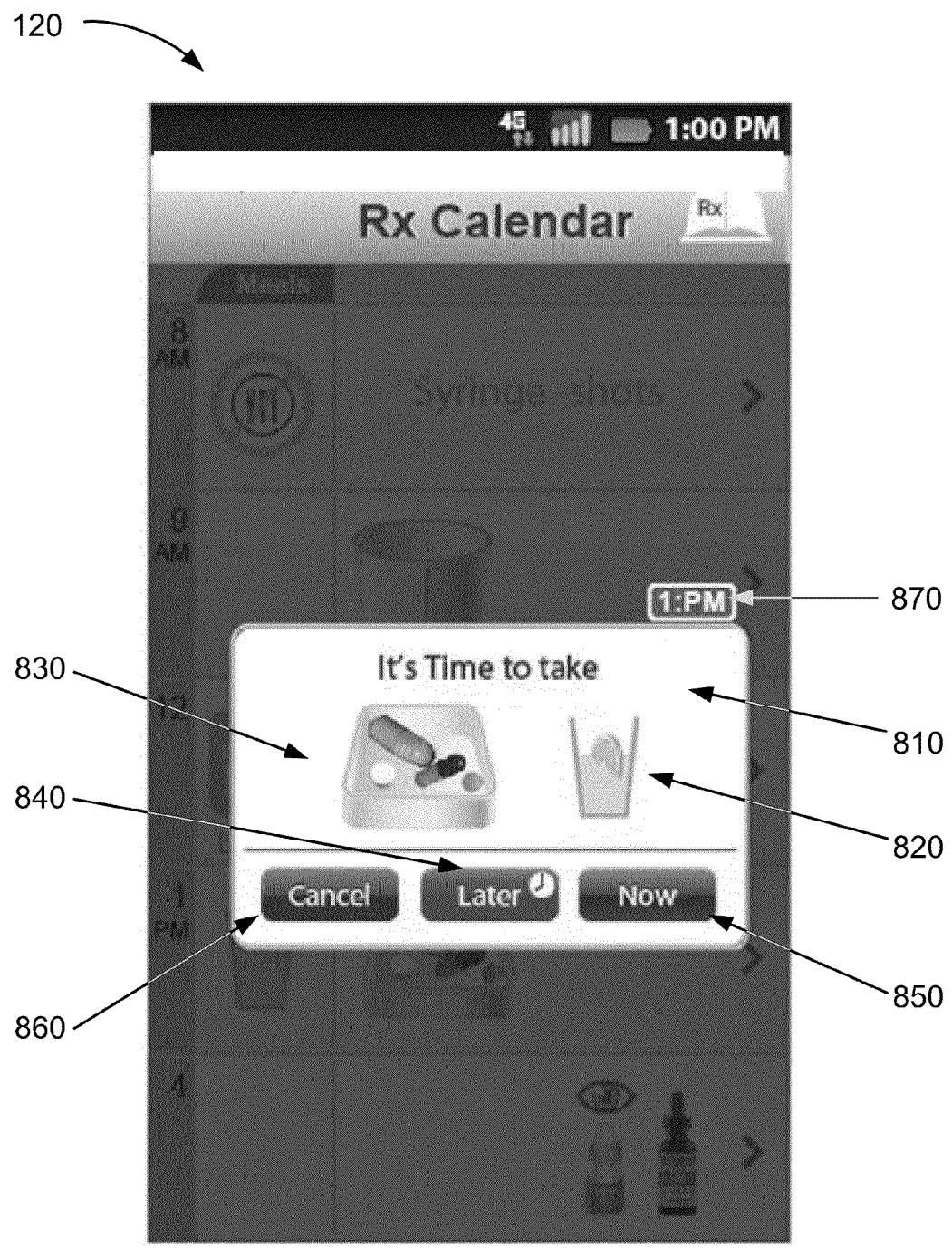
FIG. 8A is a diagram of another example user interface displaying a reminder for an example system described herein.

Returning to FIG. 4B, process 450 can provide a graphical reminder to take drugs at preset (or delayed or later times, which will be discussed further below) (block 465). For example, a graphical pop-up screen can be displayed, as illustrated in FIG. 8A. FIG. 8A is a diagram of another example user interface displaying a reminder for an example system described herein. In FIG. 8A, an example reminder 810 can be provided on the user interface 120 as a pop-up or other visual or audio cue. In this example, reminder 810 and condition 820, which in this example is "to be taken with juice," along with the drugs 830 (which can include each of the pills that are prescribed to be taken at that time) can be shown as a single reminder. The reminder 810 can be interactive or static.

Figure 9:
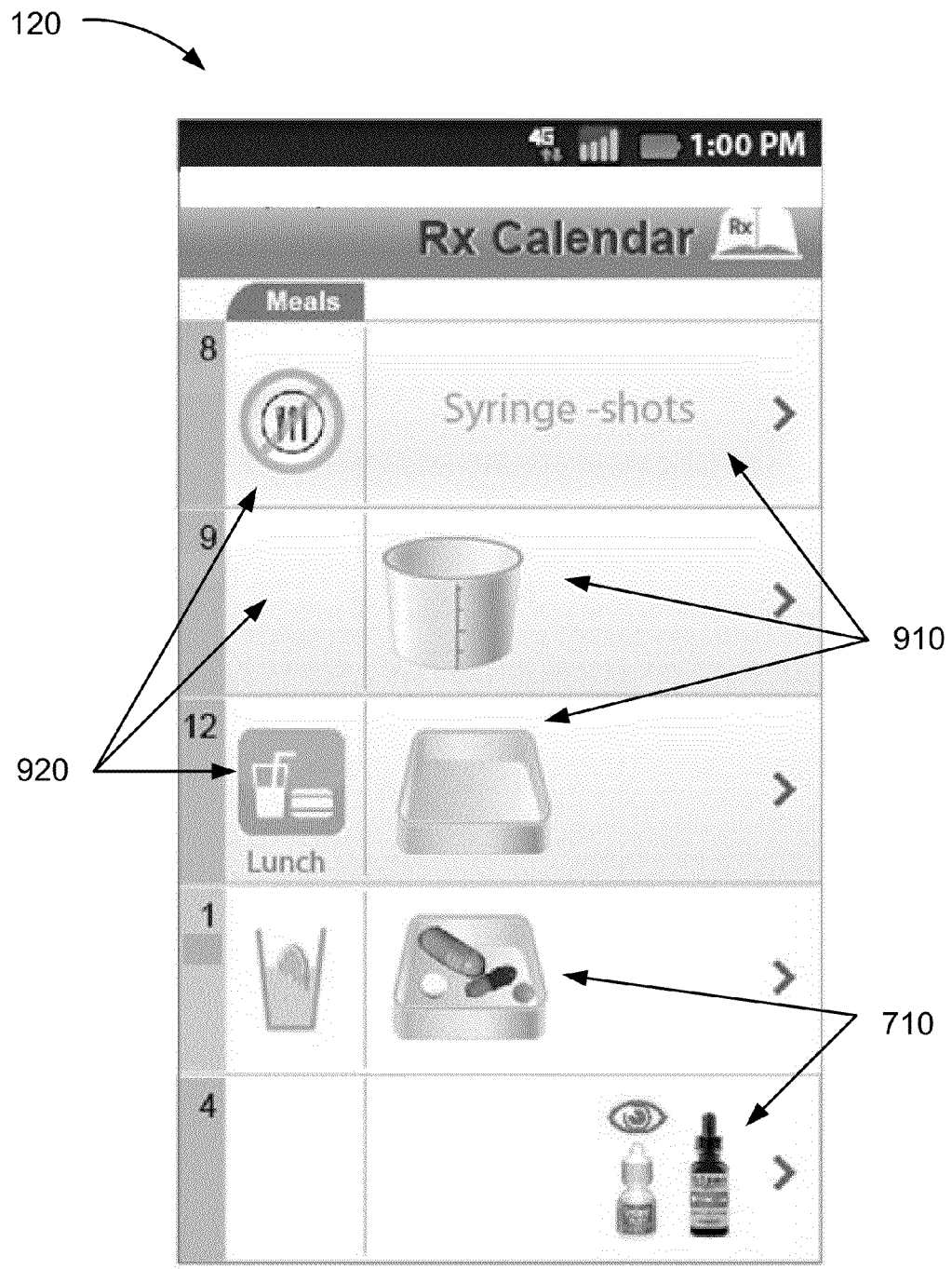
FIG. 9 is a diagram of another example user interface displaying a calendar entry for an example system described herein.

Returning to FIG. 4B, process 450 can prompt the user to indicate whether drugs were taken, partially taken, delayed, missed, or cancelled (block 470). Referring again to FIG. 8A, for example, reminder 810 can include an interactive section, which allows the drug calendar and reminder system to receive a user's input about whether drugs were taken, partially taken, delayed, missed, or cancelled. For example, in this illustration, the drug calendar and reminder system provides a user interface with interactive input buttons with the example choices of "Later" 840, which can set a delay timer to remind the user again later, "Now" 850, which can change the graphics to "empty the tray" as shown in FIG. 9, and "Cancel" 860, which cancels the reminder. This reminder 810 can also show a time 870 at which the reminder was set to appear.

Figure 8B:
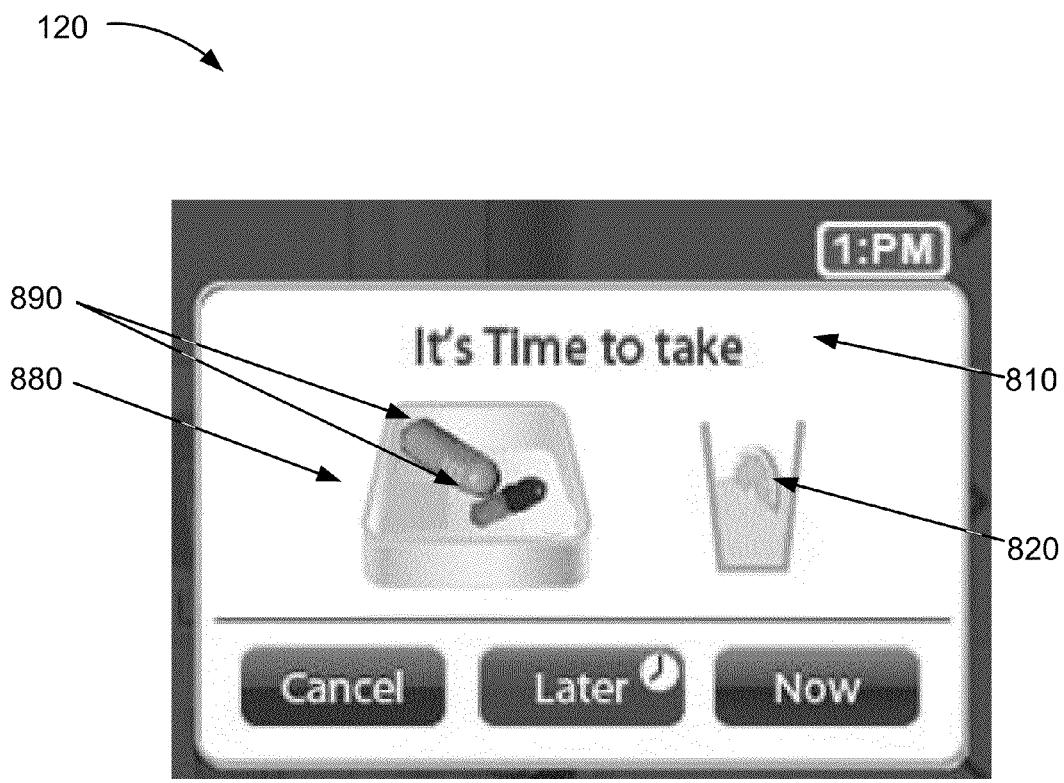
FIG. 8B is a diagram of another example user interface displaying a follow-up reminder for an example system described herein.

Further to this example, the interactive section can allow for receiving a user input of partially taking the drugs at the prescribed time. FIG. 8B is a diagram of another example user interface displaying a follow-up reminder for an example system described herein. As illustrated in FIG. 8B, after the drug calendar and reminder system receives information that the two round pills were taken (and thus removed from tray 880), the reminder 810 can be revised to reflect that only the two elongated pills 890 remain in the tray 880 (to be taken under the same condition of taking the drugs with juice 820). In this example, by providing a revised reminder 810, the user can be reminded that only the two elongated pills still need to be taken when the revised reminder 810 is displayed.

Upon receipt of an indication from the user, the drug calendar and reminder system can modify the calendar and the reminder to reflect the status of the drugs taken. FIG. 9 is a diagram of another example user interface displaying a calendar entry for an example system described herein. For example, if the drug calendar and reminder system receives an input that the drugs were taken at their prescribed times in block 470, this can be reflected in a calendar, as shown in FIG. 9, which shows that drugs 910 were taken at their appointed times 920. Additionally, the calendar can be revised to illustrate that the drugs were taken 910 (graphical entries of cups and trays appearing to be emptied) at previous set times 920 (grayed out) prior to the current time.

Figure 10:
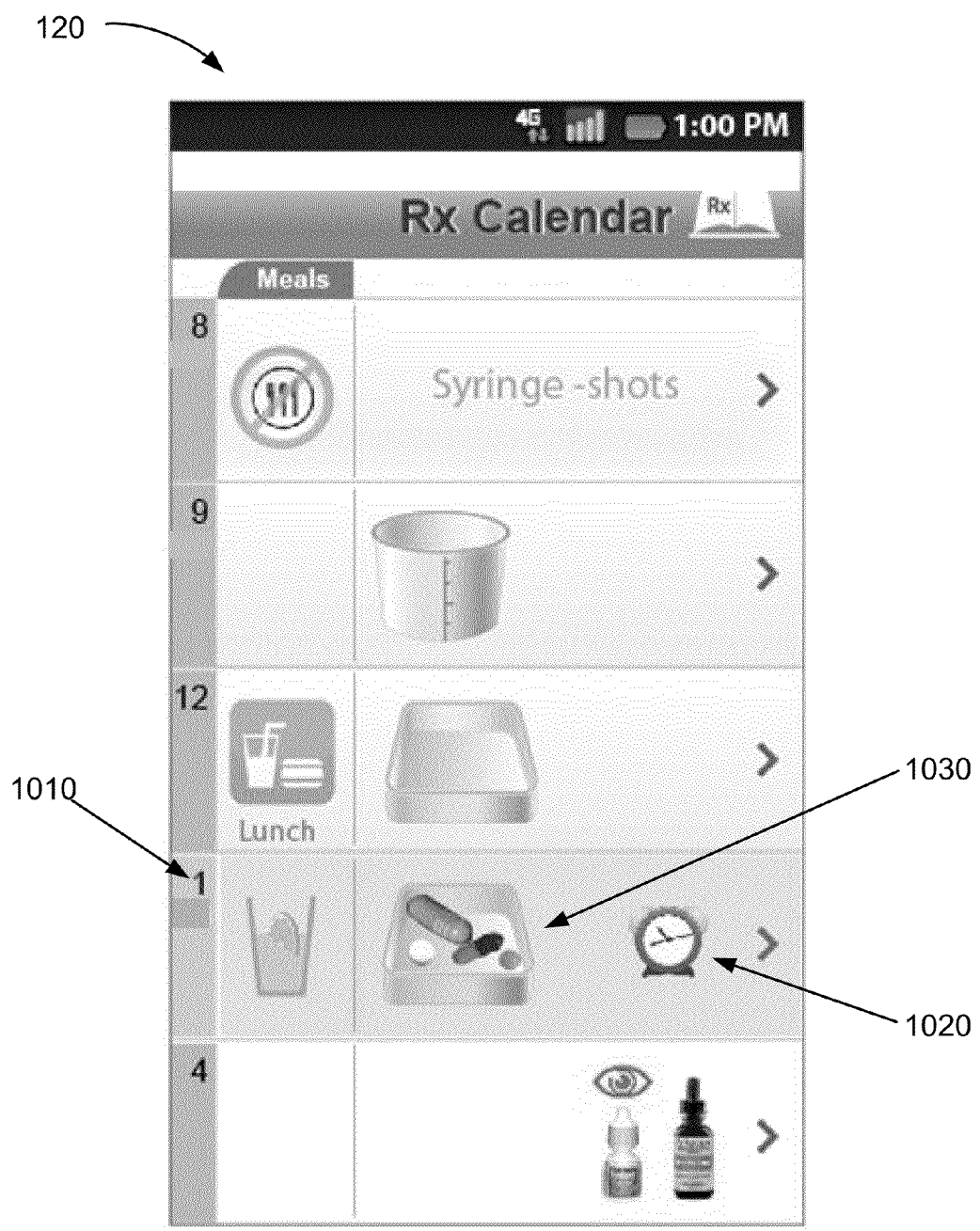
FIG. 10 is a diagram of another example user interface displaying a calendar entry including an example delayed reminder icon for an example system described herein.

As another example, if the drug calendar and reminder system receives an input that the drugs would be delayed in block 470, then the user interface 120 on the device 110 can re-display the delayed drugs at a later time as a further reminder in block 480. FIG. 10 is a diagram of another example user interface displaying a calendar entry including an example delayed reminder icon for an example system described herein. This can also be reflected in a calendar, as shown in FIG. 10, which shows that drugs 1030 were delayed along with an example icon 1020 that indicates that the user delayed the reminder from the appointed time 1010.

Figure 11:
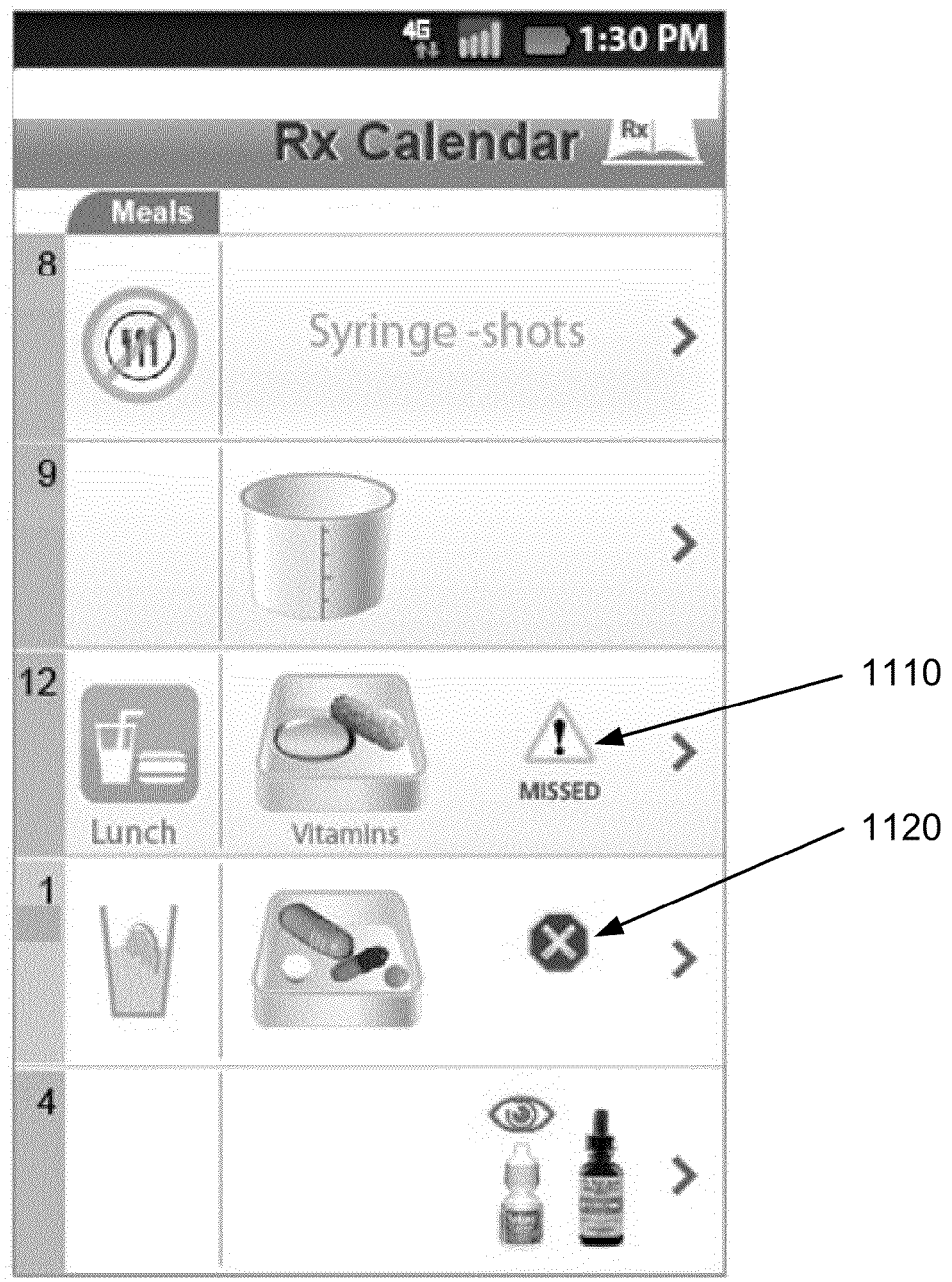
FIG. 11 is a diagram of another example user interface displaying a calendar entry including an example missed icon and an example cancelled icon for an example system described herein.

If the drug calendar and reminder system receives information that the drugs were taken, partially taken, missed, or cancelled, then the graphics can be changed to taken, partially taken, missed, or cancelled in block 475 and the drugs can be taken off reminder for this example. FIG. 11 is a diagram of another example user interface displaying a calendar entry including an example missed icon and an example cancelled icon for an example system described herein, where other icons representing partially taken, for example, can also be displayed along with the updated drug taking status (i.e., which drugs were taken and which drugs remain to be taken). FIG. 11 illustrates an example graphical representation of times at which one dosing was missed 1110 and another was cancelled 1120 as discussed concerning blocks 470, 480, and 485 of FIG. 4B. As illustrated in FIG. 11, a missed drug dosing can be graphically represented by an example "MISSED" word along with an icon 1110, and a cancelled drug dosing can be represented by an example "cancelled" icon 1120 indicating that the reminder for the drugs was cancelled. As shown, these example icons can include words or may just be graphical icons including but not limited to those shown herein.

Additionally, if the drug calendar and reminder system receives information that the drugs were partially taken or missed (and not cancelled), then further reminders can be automatically set by the drug calendar and reminder system. For example, if a drug dosage was missed 1110, as illustrated in FIG. 11, a reminder similar to FIG. 8A, if missed, or FIG. 8B, if partially taken, can be automatically scheduled for ease of use.

Figure 12:
FIG. 12 is a diagram of another example user interface displaying a calendar entry with example links to more information for an example system described herein.

FIG. 12 is a diagram of another example user interface displaying a calendar entry with example links to more information for an example system described herein. FIG. 12 illustrates example link icon 1210 that a user can select to show more information on the user interface 120. Example link icon 1210 can be used to show information linked to the drugs taken at 8, for example. In FIG. 12, link icon 1210 can be used to request or show information on the syringes 1220 shown adjacent to the link icon 1210.

Figure 13:
FIG. 13 is a diagram of another example user interface displaying calendar entries for an example caregiver with multiple patients for an example system described herein.
Figure 14:
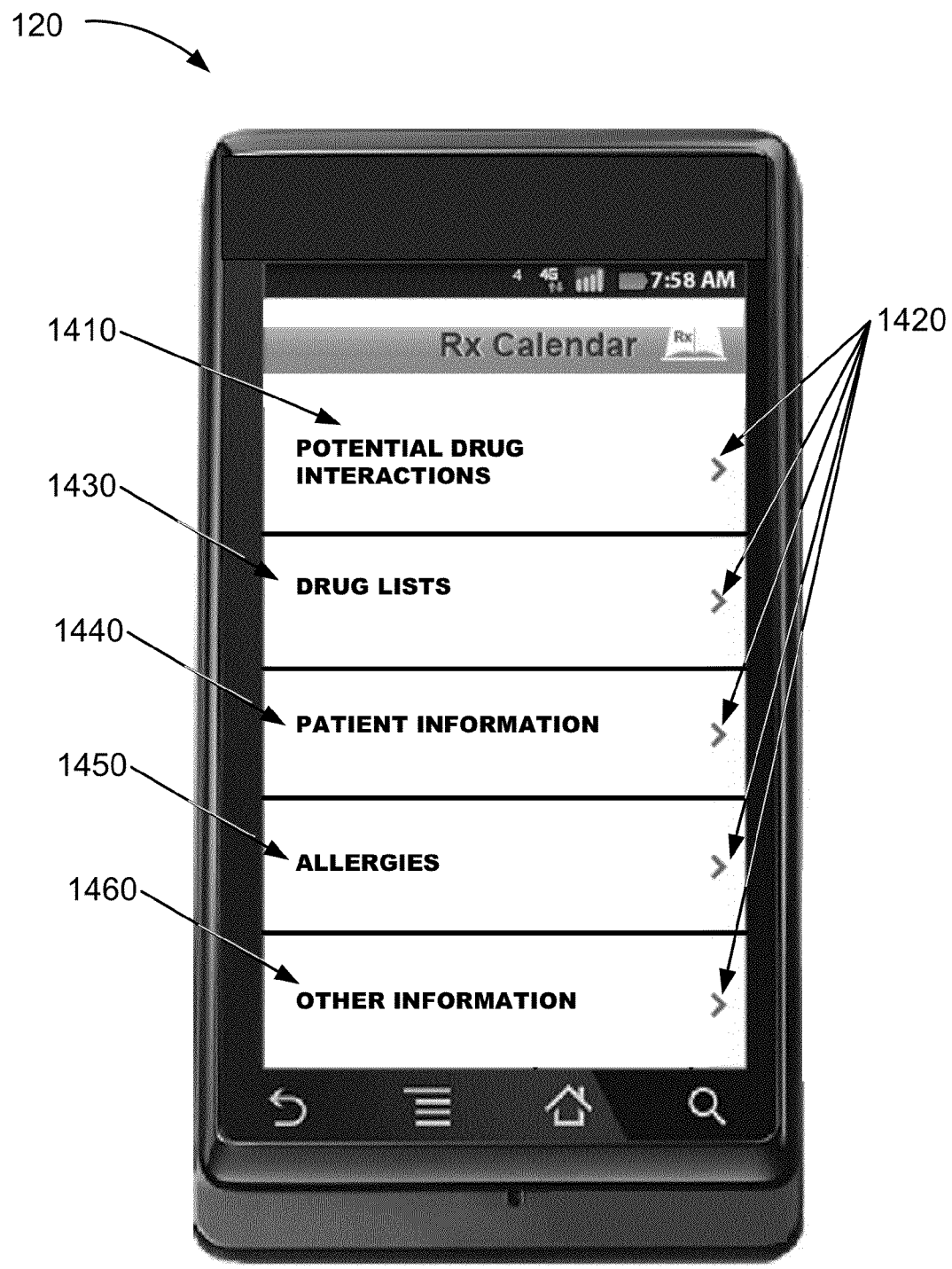
FIG. 14 is a diagram of another example embodiment of an interface displaying an example list of information for an example system described herein.

FIG. 13 illustrates an example user interface 120 displaying calendar entries that can be used by an example caregiver of multiple patients. In this example, a first patient "A" 1310 and a second patient "B" 1320 can have their drug calendar and reminder systems on a single user interface 120 of a caregiver. Also in this example, a link icon 1330 can provide information for each of the patients for the user (caregiver) or patient's information similar to link 1220 as discussed above. The other link icon 1340 can be used to access a list or additional user interface, as illustrated in FIG. 14, that can show general information about the drug list, such as potential adverse drug interactions that may occur with any of the drugs currently being taken, about the user or patient(s), such as insurance policies, vital statistics, address, emergency contacts, allergies, or other information that can be found quickly by the user if desired. For example, at 8, when second patient "B" 1320 is scheduled to take their syringes, link icon 1350 can link to additional information either on the syringe or patient "B" 1320, while at 9, when patient "A" 1310 takes a vial of liquid, link icon 1360 can link to additional information either on the liquid or on patient "A" 1310.

FIG. 14 is a diagram of another example embodiment of an interface displaying an example list of information. FIG. 14 illustrates an example list that can list information and link icons that can provide more information for the list entries. This example list can be accessed through the user interface such as by activating link 1340, for example. The example list can include potential drug interactions 1410, further information links 1420, drug lists 1430, patient information 1440, such as insurance policies, vital statistics, address, emergency contacts, allergies, and patient allergies 1450, such as allergies to penicillin, as well as link icons 1420 for more information or for other information 1460 that the user of device 110 might find useful.

The foregoing description provides illustration and description, but is not intended to be exhaustive or to limit the implementations to the precise form disclosed. Modifications and variations are possible in light of the above disclosure or may be acquired from practice of the implementations.

It will be apparent that different aspects of the description provided above may be implemented in many different forms of software, firmware, and hardware in the implementations illustrated in the figures. The actual software code or specialized control hardware used to implement these aspects is not limiting of the implementations. Thus, the operation and behavior of these aspects were described without reference to the specific software code—it being understood that software and control hardware can be designed to implement these aspects based on the description herein.

Even though particular combinations of features are recited in the claims or disclosed in the specification, these combinations are not intended to limit the disclosure of the possible implementations. In fact, many of these features may be combined in ways not specifically recited in the claims or disclosed in the specification. Although each dependent claim listed below may directly depend on only one other claim, the disclosure of the possible implementations includes each dependent claim in combination with every other claim in the claim set.

No element, act, or instruction used in the present application should be construed as critical or essential unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method, comprising:
    presenting, via a display associated with a device, a first user interface to permit a user to specify a drug;
    receiving, from the user via the first user interface, input specifying the drug;
    storing, in a memory associated with the device, the input specifying the drug;
    presenting, via the display associated with the device, a second user interface to permit a user to specify dosing information,
        the dosing information identifying:
            a dosage time, and
            a dosage condition;
    receiving, from the user via the second user interface, input specifying the dosing information for the drug;
    storing, in the memory associated with the device, the dosing information for the drug;
    receiving, by a processor of the device, an instruction from the user of the device to prepare a calendar using the input specifying the drug and the dosing information;
    preparing, by the processor of the device, a calendar using the input specifying the drug and the dosing information;
    receiving, by the processor of the device, an instruction to display the calendar;
    providing, via the display, a graphical user interface of the calendar that includes a graphical representation of the drug and at least one of a graphical representation of a container associated with the drug or a graphical representation of an ingestion method associated with the drug;
    modifying, based on receiving information indicating that the drug was partially taken, the graphical representation of the drug to visually represent only a remaining portion of the drug to be taken; and
    revising the graphical user interface of the calendar to include the modified graphical representation of the drug.

2. The method of claim 1, where receiving, from the user via the first user interface, the input specifying the drug includes:
    presenting, via the first user interface, an interactive input area in which the user can enter a portion of a drug name;
    receiving the portion of the drug name via the interactive input area;
    presenting, via the first user interface, images of possible drugs based on the portion of the drug name; and
    receiving a selection of the drug from the images of possible drugs presented via the first user interface.

3. The method of claim 1, where receiving, from the user via the first user interface, the input specifying the drug includes:
    presenting the first user interface to enable the user to select the drug along with the dosage time and the dosage condition from a list or a set of icons; and
    where receiving the dosing information includes:
        receiving a selection, via the first user interface, of the drug, the dosage time and the dosage condition.

4. The method of claim 1, further comprising:
    preparing a reminder associated with the drug based on the dosing information; and
    providing, via the display, the reminder at a time indicated by the dosing information.

5. The method of claim 4, further comprising:
receiving, based on providing the reminder, the information indicating that the drug was partially taken.

6. The method of claim 4, further comprising:
receiving, based on providing the reminder, the information indicating that the drug was partially taken;
preparing an additional reminder based on the information indicating that the drug was partially taken; and
providing the additional reminder for display,
the additional reminder including the modified graphical representation of the drug, and
the additional reminder indicating that the drug was partially taken.

7. The method of claim 4, further comprising:
presenting a visual notification reminder comprising the graphical representation of the drug and the dosing information via the display, or
presenting an audible notification reminder associated with the drug and the dosing information via a speaker associated with the device.

8. The method of claim 1, further comprising:
preparing a reminder based on the information indicating that the drug was partially taken; and
providing the reminder for display,
the reminder including the modified graphical representation of the drug.

9. The method of claim 1, where receiving the input specifying the dosing information for the drug further includes:
receiving, from a content provider, additional dosing information,
the additional dosing information including content provider information for the drug; and
where the providing the graphical user interface of the calendar includes:
providing a graphical representation of the content provider information for the drug in a visual calendar format,
where the content provider information includes one or more of:
drug interaction information from a drug interaction server,
drug database information from a drug database server,
medical information from a doctor server, or
pharmacy dosing information from a pharmacy server.

10. The method of claim 9, further comprising:
compiling a list of the drug, a dosage time, a dosage condition, and the content provider information;
transmitting the list to the drug interaction server, the doctor server, or the pharmacy server; and
receiving, based on transmitting the list, information regarding adverse interactions between the drug and another drug associated with the user from the drug interaction server, the doctor server, or the pharmacy server.

11. The method of claim 1, further comprising:
presenting a third user interface to permit the user to specify another drug for an additional person;
receiving an input specifying the other drug;
storing the input specifying the other drug;
presenting a fourth user interface to permit the user to specify dosing information for the other drug;
receiving the dosing information for the other drug,
where the dosing information for the other drug includes a dosage time and a dosage condition for the other drug;
storing the dosing information for the other drug;
receiving an instruction to prepare a shared calendar including the drug and the other drug for the additional person based on the dosing information for the drug and the dosing information for the other drug;
preparing the shared calendar;
receiving an instruction to provide the shared calendar for display; and
providing the shared calendar for display based on the instructions,
the shared calendar including the graphical representation of the drug and a graphical representation of the other drug in a visual calendar format.

12. A method, comprising:
presenting, by a processor of a device and via a display associated with the device, an interactive input area in which a user can enter a portion of a drug name;
receiving, by the processor, the portion of the drug name via the interactive input area;
presenting, by the processor and via a first user interface, images of possible drugs based on the portion of the drug name;
receiving, by the processor and from the user via the first user interface, a selected drug image from the images of possible drugs presented via the first user interface,
the selected drug image specifying a drug;
storing, by the processor and in a memory associated with the device, the selected drug image and information identifying the drug;
presenting, by the processor and via the display, a second user interface;
receiving, by the processor and via the second user interface, input specifying dosing information associated with the drug,
the dosing information including:
information indicating a dosage time associated with the drug, and
information indicating a dosage condition associated with the drug;
storing, by the processor and in the memory, the dosing information;
preparing a first reminder associated with the drug based on the dosing information;
providing, based on the dosage time, the first reminder for display,
the first reminder comprising the selected drug image, a graphical representation of a container associated with the drug, and a graphical representation of an ingestion method associated with the drug;
modifying, based on information indicating that the drug was partially taken, the selected drug image to visually represent only a remaining portion of the drug to be taken; and
providing a second reminder for display, the second reminder including the modified selected drug image.

13. The method of claim 12, further comprising:
presenting a third user interface for display;
receiving the information indicating that the drug was partially taken via the third user interface;
preparing a calendar based on the information indicating that the drug was partially taken; and
providing the calendar for display,
the calendar including the modified selected drug image to indicate that the drug was partially taken.

14. The method of claim 12, further comprising:
receiving an input indicating that another drug was taken;
preparing a calendar based on the information indicating that the drug was partially taken and the input indicating that the other drug was taken; and
providing the calendar for display,
the calendar including a graphical representation indicating that the other drug was taken, and the modified selected drug image.

15. The method of claim 12, where providing the first reminder for display includes:
presenting an audible notification reminder associated with the drug and the dosing information via a speaker associated with the device.

16. The method of claim 12, where receiving the input specifying the dosing information for the drug includes:
receiving, from a content provider, additional dosing information,
the additional dosing information including information identifying a dosage time associated with the drug, information indicating a dosage condition associated with the drug, and content provider information for the drug; and
where the providing the first reminder includes:
providing a graphical user interface reminder that includes a graphical representation of the content provider information for the drug in a visual reminder format,
where the content provider information includes drug interaction information from a drug interaction server, drug database information from a drug database server, medical information from a doctor server, or pharmacy dosing information from a pharmacy server.

17. The method of claim 12, further comprising:
presenting a third user interface to permit the user to specify another drug for an additional person;
receiving input specifying the other drug;
storing the input specifying the other drug;
presenting a fourth user interface to permit the user to specify dosing information for the other drug for the additional person;
receiving the dosing information for the drug,
where the dosing information includes a dosage time and a dosage condition;
storing the dosing information for the other drug;
preparing a shared calendar,
the shared calendar including the selected drug image, an image corresponding to the other drug, the dosing information for the drug, and the dosing information for the other drug; and
providing the shared calendar for display in a visual calendar format.

18. The method of claim 12, further comprising:
receiving an instruction from the user of the device to prepare a calendar including the selected drug image and the dosing information;
determining that the calendar is scheduled to be displayed; and
providing a graphical user interface calendar comprising the selected drug image and a graphical representation of the dosing information.

19. A non-transitory computer-readable medium storing instructions, the instructions comprising:
a plurality of instructions which, when executed by at least one processor, cause the at least one processor to:
present a user interface to permit a user to specify drugs for at least two people;
receive an input specifying the drugs;
store the input specifying the drugs;
receive dosing information for the drugs,
the dosing information including information identifying dosage times associated with the drugs and dosage conditions associated with the drugs;
store the dosing information for the drugs;
prepare a calendar using the input specifying the drugs and the input specifying the dosing information for the drugs;
receive an instruction to display the calendar;
provide the calendar for display based on the instructions,
the calendar including graphical representations of the drugs, graphical representations of the dosing information, a graphical representation of a respective container associated with each of the drugs, and graphical representations of a respective ingestion method associated with each of the drugs;
prepare reminders associated with the drugs;
determine, based on the dosing information, that one of the reminders is scheduled to be displayed; and
provide, when the one of the reminder is scheduled to be displayed, a graphical user interface reminder comprising a graphical representation of one of the drugs, the dosing information associated with the one of the drugs, the respective container associated with the one of the drugs, and the respective ingestion method associated with the one of the drugs.

20. The non-transitory computer-readable medium of claim 19, where the plurality of instructions further cause the at least one processor to:
receive, from a content provider, additional dosing information,
the additional dosing information including input specifying dosage times, dosage conditions, and content provider information for the drugs,
where the content provider information includes drug interaction information from a drug interaction server, drug database information from a drug database server, medical information from a doctor server, or pharmacy dosing information from a pharmacy server; and
provide a graphical representation of the content provider information for the drugs for display.

21. The non-transitory computer-readable media of claim 19, where the plurality of instructions further cause the at least one processor to:
modify, based on information indicating that the one of the drugs was partially taken, the graphical representation of the one of the drugs to visually present only a remaining portion of the one of the drugs.

22. The non-transitory computer-readable media of claim 19, where the plurality of instructions further cause the at least one processor to:
receive a selection of an image of a generic container to be associated with the one of the drugs,
where the graphical representation of the container corresponds to the selected image of the generic container.

23. A system, comprising:
a device including at least one processor to:
present for display, a first user interface to permit a user to specify a drug, the first user interface presenting graphical images of
drugs for selection by the user;
receive, from the user via the first user interface, a selection of a graphical image of the drug from the graphical images of drugs;
present for display, a second user interface to permit the user to input dosing information for the drug,
the dosing information identifying:
a dosage time, and
a dosage condition;
receive, from the user via the second user interface, input specifying the dosing information;
prepare a calendar using the selected graphical image of the drug and the dosing information;
provide the calendar for display,
the calendar including the selected graphical image of the drug, a graphical representation of a container associated with the drug, and a graphical representation of an ingestion method associated with the drug;
prepare a reminder associated with the drug;
provide, when the reminder is scheduled to be displayed, the reminder associated with the drug for display;
modify, based on information that the drug was partially taken, the selected graphical image of the drug to visually represent only a remaining portion of the drug to be taken; and
revise the calendar to include the modified graphical image of the drug.

\* \* \* \* \*